US010588634B2

(12) United States Patent
Matthias et al.

(10) Patent No.: US 10,588,634 B2
(45) Date of Patent: Mar. 17, 2020

(54) SURGICAL STAPLER CARTRIDGE LOADING AND UNLOADING

(71) Applicant: AESCULAP AG, Tuttlingen (DE)

(72) Inventors: Benjamin J. Matthias, Emerald Hills, CA (US); Kevin L. Hudelson, Redwood City, CA (US); Nicholas J. Terzulli, Union City, CA (US); Thomas J. Palermo, San Jose, CA (US); Julian N. Nikolchev, Portola Valley, CA (US)

(73) Assignee: Aesculap AG (DE)

( * ) Notice: Subject to any disclaimer, the term of this patent is extended or adjusted under 35 U.S.C. 154(b) by 225 days.

(21) Appl. No.: 15/646,524

(22) Filed: Jul. 11, 2017

(65) Prior Publication Data

US 2019/0015101 A1    Jan. 17, 2019

(51) Int. Cl.
| | |
|---|---|
| *A61B 17/072* | (2006.01) |
| *A61B 50/00* | (2016.01) |
| *A61B 17/068* | (2006.01) |
| *A61B 90/00* | (2016.01) |
| *A61B 17/00* | (2006.01) |
| *A61B 50/22* | (2016.01) |
| *A61B 17/064* | (2006.01) |
| *A61B 34/30* | (2016.01) |

(52) U.S. Cl.
CPC .... *A61B 17/07207* (2013.01); *A61B 17/0644* (2013.01); *A61B 34/30* (2016.02); *A61B 50/00* (2016.02); *A61B 50/22* (2016.02); *A61B 2017/0053* (2013.01); *A61B 2017/0688* (2013.01); *A61B 2017/07221* (2013.01); *A61B 2017/07257* (2013.01); *A61B 2017/07271* (2013.01); *A61B 2017/07278* (2013.01); *A61B 2090/037* (2016.02)

(58) Field of Classification Search
None
See application file for complete search history.

(56) References Cited

U.S. PATENT DOCUMENTS

| | | | |
|---|---|---|---|
| 3,662,939 A * | 5/1972 | Bryan | A61B 17/0684 227/19 |
| 5,533,521 A * | 7/1996 | Granger | A61B 90/06 600/587 |
| 7,988,026 B2 | 8/2011 | Knodel et al. | |
| 9,004,339 B1 | 4/2015 | Park | |

(Continued)

*Primary Examiner* — Hemant Desai
*Assistant Examiner* — Tanzim Imam
(74) *Attorney, Agent, or Firm* — RatnerPrestia

(57) ABSTRACT

An exemplary surgical method includes possessing a loader that holds a curved-tip cartridge, and a surgical stapler that includes an anvil and channel at a distal end thereof; causing at least one of the loader and the channel to move toward the other; as a result of the causing, engaging the loader and the curved-tip cartridge with the channel; and causing at least one of the loader and the channel to move away from the other, such that the curved-tip cartridge remains engaged with the channel. That method further may include actuating the surgical stapler; grasping the unloader; sliding the unloader toward the channel; disengaging the curved-tip cartridge from the channel with the unloader; and withdrawing the unloader away from said channel, wherein the withdrawing causes the curved-tip cartridge to disengage from the channel.

7 Claims, 14 Drawing Sheets

(56) References Cited

U.S. PATENT DOCUMENTS

2003/0040759 A1\*  2/2003  de Guillebon ..... A61B 17/1285
                                                606/142
2017/0105751 A1\*  4/2017  Hibner ........... A61B 17/320092

\* cited by examiner

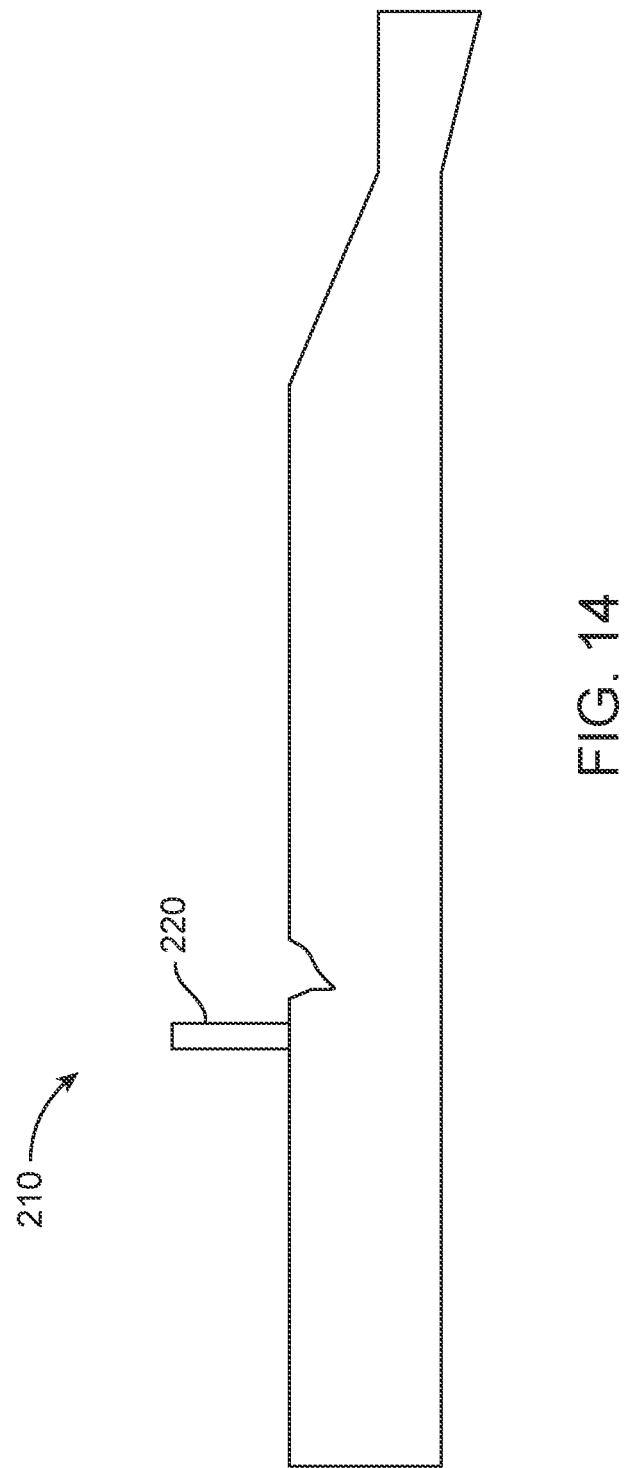

SURGICAL STAPLER CARTRIDGE LOADING AND UNLOADING

FIELD OF THE INVENTION

The invention generally relates to surgical staplers and stapling.

BACKGROUND

A surgical stapler both staples and cuts tissue to transect that tissue while leaving the cut ends hemostatic. A typical surgical stapler receives at its distal end a disposable single-use cartridge with several rows of staples, and includes an anvil opposed to the cartridge.

Conventional surgical staplers have an anvil with a straight or curved distal end. However, with the exception of surgical stapler cartridges manufactured by Dextera Surgical Inc. of Redwood City, Calif., all conventional surgical stapler cartridges on the market today have a straight distal end. Surgeons, nurses, technicians, and/or other personnel in the operating room may be hesitant to load or unload curved-tip staple cartridges into a surgical stapler by hand, as they are largely unfamiliar with such cartridges. Thus, there is a need to simplify the process of loading and unloading curved-tip staple cartridges such that the user has more confidence in handling those curved-tip cartridges.

BRIEF DESCRIPTION OF THE DRAWINGS

FIG. 14 is a side view of a combination loader/unloader.

The use of the same reference symbols in different figures indicates similar or identical items.

DETAILED DESCRIPTION

Loader

Figure 1:
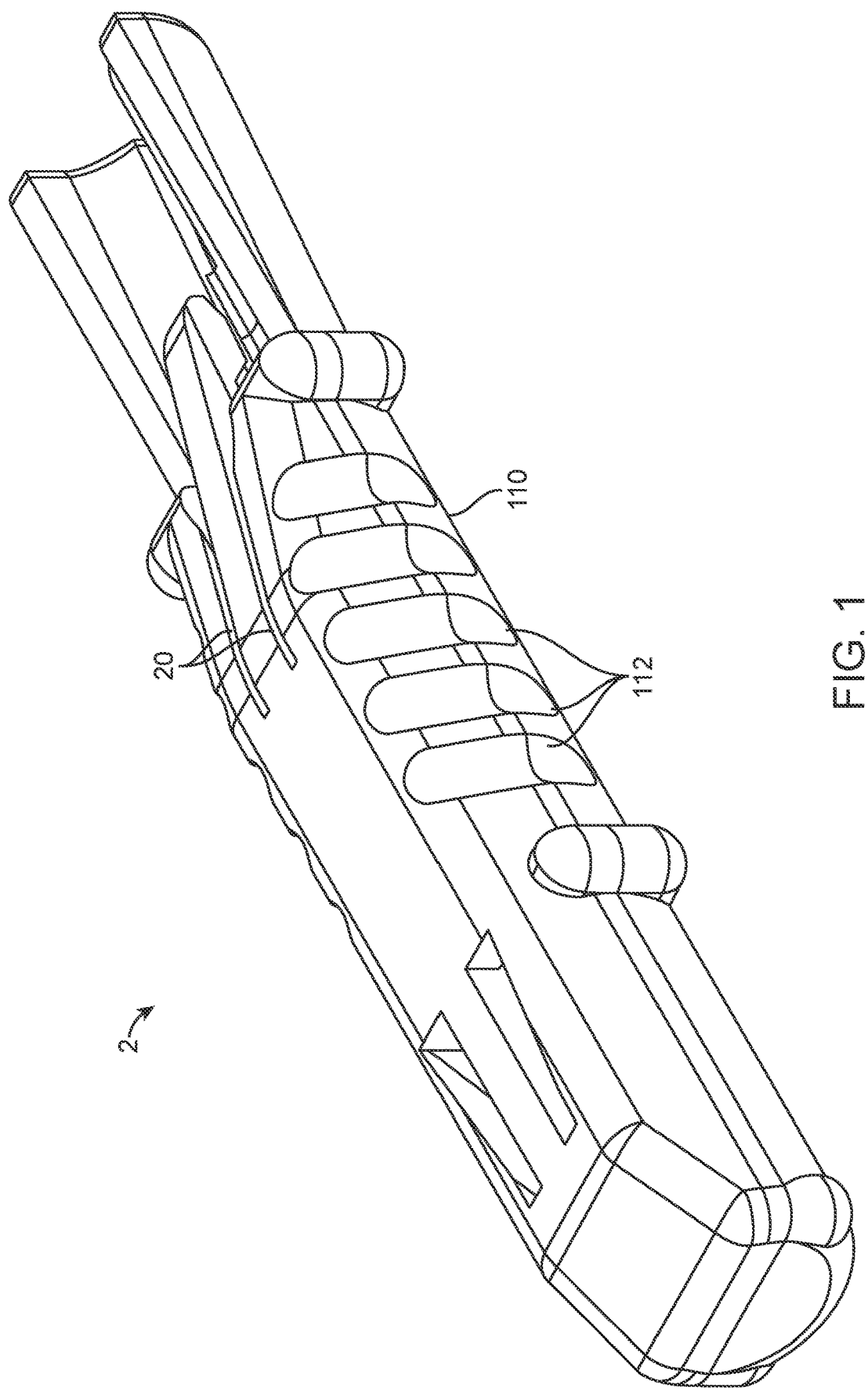
FIG. 1 is a perspective view of an exemplary loader.
Figure 2:
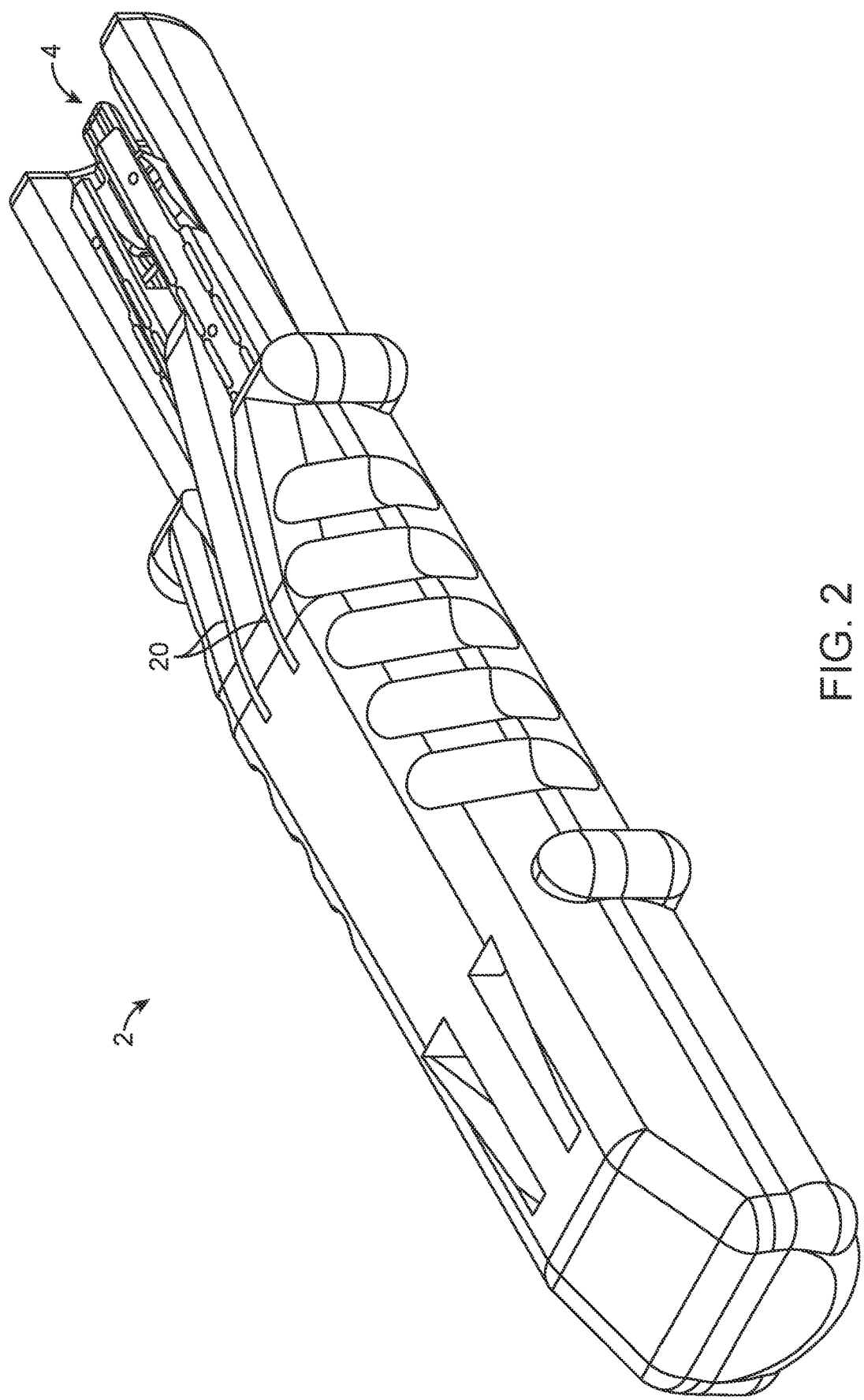
FIG. 2 is a perspective view of the exemplary loader of FIG. 1 with a cartridge held thereby.
Figure 3:
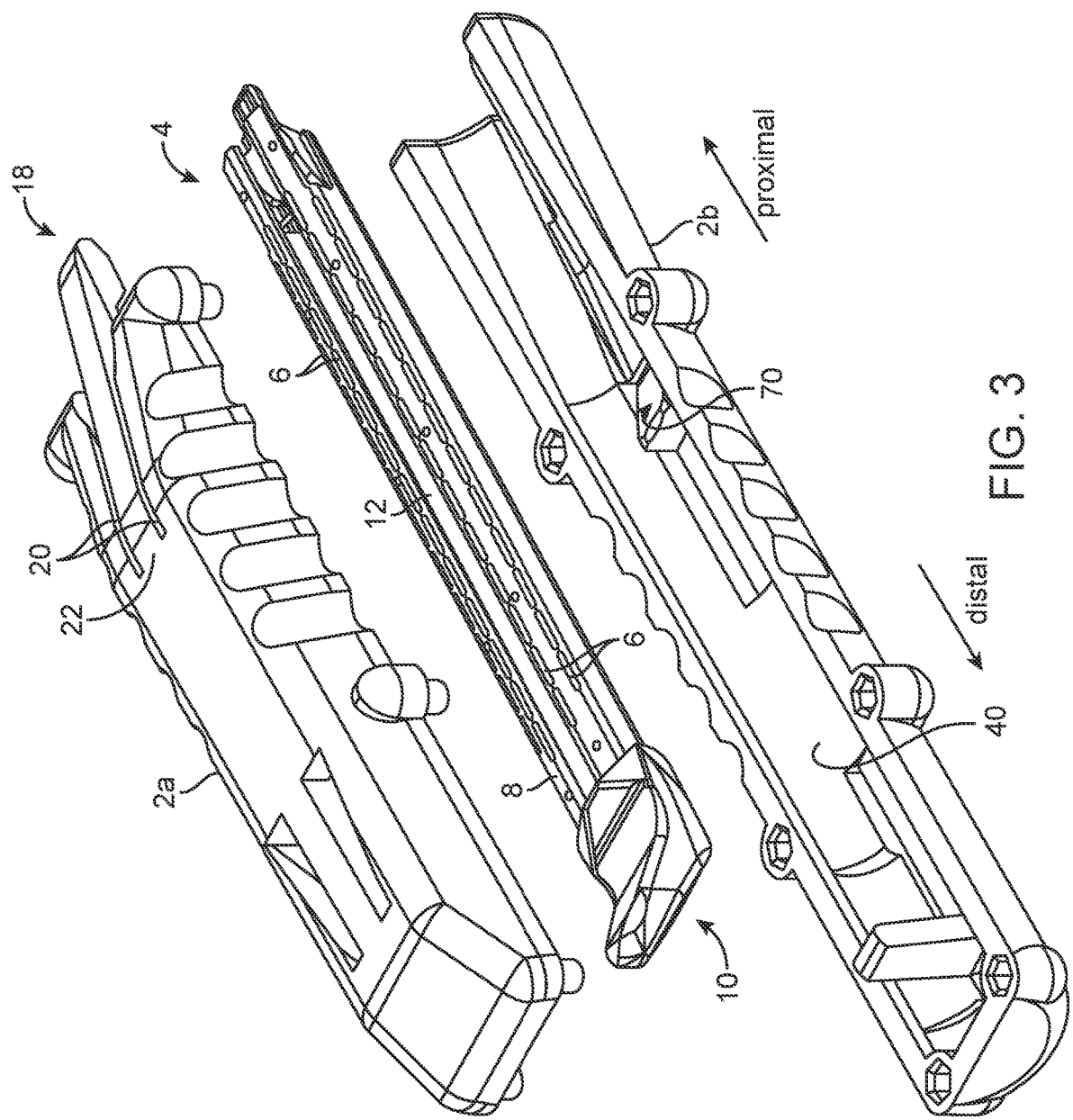
FIG. 3 is an exploded view of FIG. 2.

Referring to FIGS. 1-3, a loader 2 is shown. The loader 2 provides an ergonomic and simple way to insert a curved-tip cartridge 4 into a stapler channel.

As seen in FIG. 3, the loader 2 may be fabricated as a two-piece component, with an upper loader body 2a and a lower loader body 2b. The two loader components 2a, 2b may be attached to one another by adhesive, by fasteners, and/or in any other suitable manner. The components 2a, 2b may be fabricated by injection molding, additive manufacturing (colloquially referred to as "3-D printing"), by stamping, or by any other suitable process. Alternately, the loader 2 may be fabricated as a single component in any suitable manner, such as by additive manufacturing. The upper loader body 2a and lower loader body 2b may be referred to collectively as a body.

In some embodiments, the cartridge 4 may hold one or more staple strips with staples frangibly affixed thereto, as described in commonly-assigned U.S. Pat. No. 7,988,026, which is hereby incorporated by reference in its entirely. In such embodiments, the staples may be configured for direct contact with a wedge, and the cartridge 4 does not include conventional staple drivers, as described in commonly-assigned U.S. Pat. No. 7,988,026. Alternately, in other embodiments, the cartridge 4 holds conventional U-shaped surgical staples and conventional staple drivers, arranged such that motion of a wedge relative to a staple driver causes the staple driver to contact a corresponding staple and urge that staple toward an anvil. The cartridge 4 may include any suitable number of rows of staples, corresponding to rows of staple openings 6 on the upper surface 8 of the cartridge 4. As shown in FIG. 2, as one example the cartridge 4 includes four rows of staple openings 6, the rows extending longitudinally and substantially parallel to one another, with two rows on each side of the longitudinal centerline of the cartridge 4. In other embodiments, the cartridge 4 may include any other number of rows of staple openings 6, arranged symmetrically or asymmetrically. For example, the cartridge 4 may include six rows of staple openings 6, with three rows on each side of the longitudinal centerline of the cartridge 4, as in a conventional surgical staple cartridge. The upper surface 8 of the cartridge 4 may have any suitable shape or orientation, and may include two or more planar surfaces angled relative to one another. Alternately, the upper surface 8 of the cartridge 4 may be a single substantially planar surface. The cartridge 4 may be configured as described in commonly-assigned U.S. Pat. No. 9,004,339, which is hereby incorporated by reference in its entirety.

The cartridge 4 includes a curved tip 10. The curved tip 10 is curved upward relative to the longitudinal centerline of the cartridge 4 such that the curved tip 10 terminates at a location above the upper surface 8 of the cartridge 4. The curved tip 10 may taper in width and/or thickness toward the distal direction from the junction between the curved tip 10 and the remainder of the cartridge 4. As used herein, the term "curved-tip cartridge" is defined to mean a surgical staple cartridge 4 with a curved tip at its distal end.

The cartridge 4 also may include a trough 12 defined through the upper surface 8. In some embodiments, the trough 12 extends distally from the proximal end of the cartridge 4, such that the proximal end of the cartridge 4 is open at its intersection the proximal end of the trough 12. Alternately, the trough 12 does not intersect the proximal end of the cartridge 4. The trough 12 may have any suitable length along the upper surface 8, and may extend along part or all of that upper surface 8. The trough 12 may have any suitable depth. The upper loader body 2a and lower loader body 2b collectively define a cavity 14 therein in which the cartridge 4 may be held.

Figure 4:
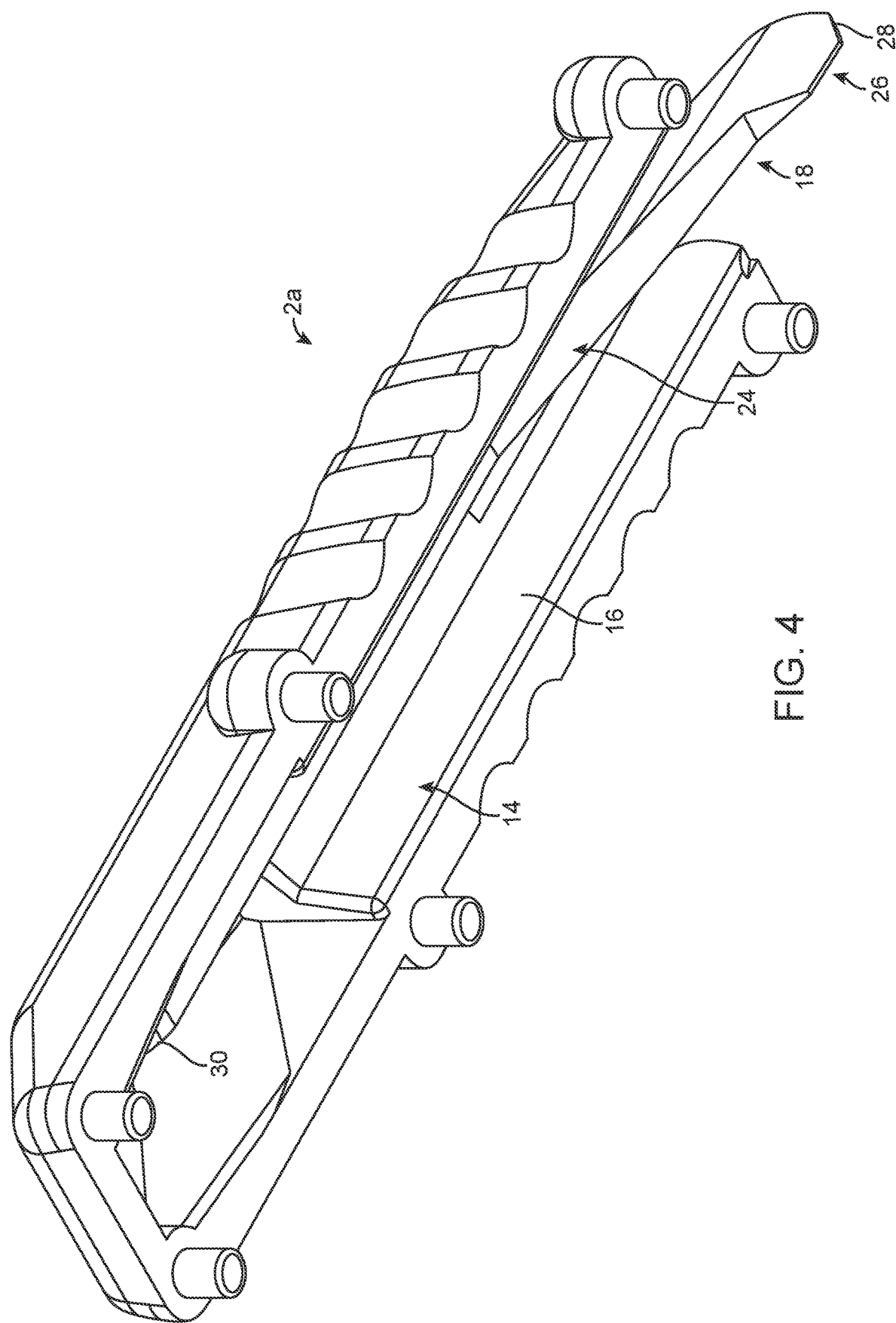
FIG. 4 is a perspective view upward into an upper loader body of the loader of FIG. 1.
Figure 5:
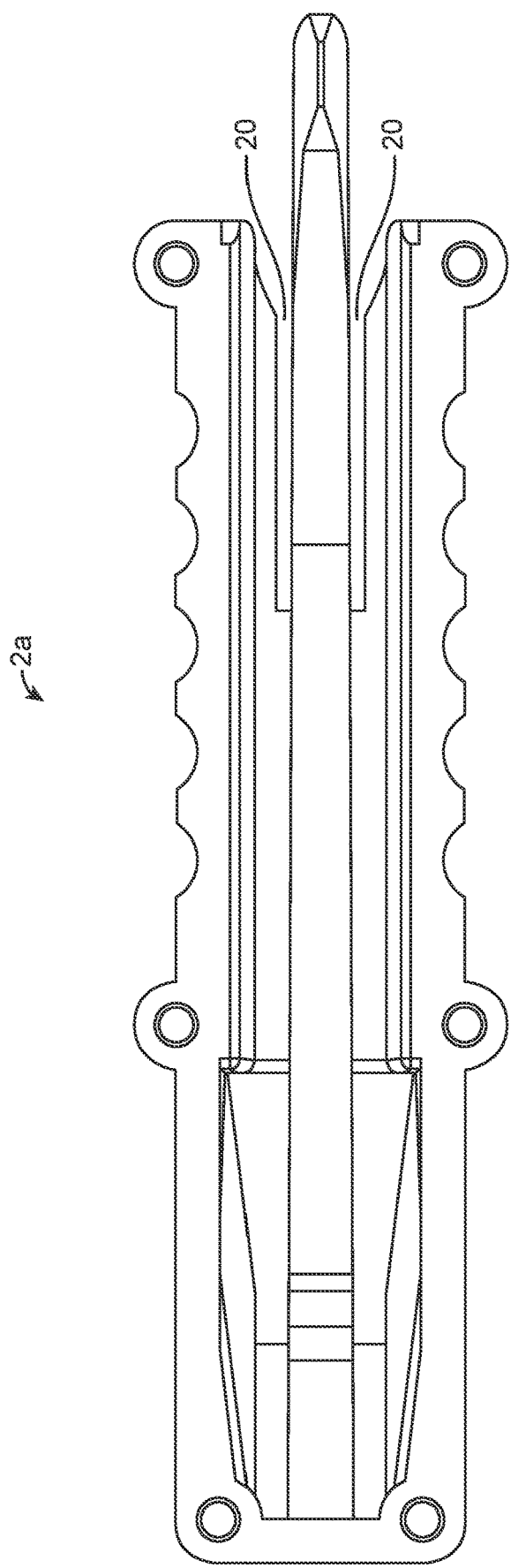
FIG. 5 is a bottom view of the upper loader body of FIG. 4.

Referring also to FIGS. 4-5, an inner surface 16 of the upper loader body 2a defines part of the cavity 14 described above. A proximal upper spring 18 is defined in the upper loader body 2a. Slots 20 may extend laterally along the lateral sides of the proximal upper spring 18, separating the lateral sides of the proximal upper spring 18 from a remainder of the upper loader body 2a. The distal end 22 of the proximal upper spring 18 may be connected to a remainder of the upper loader body 2a in any suitable manner. In one embodiment, the proximal upper spring 18 has the same thickness as the adjacent portion of the upper loader body 2a and extends proximally from the junction between the distal end 22 of the proximal upper spring 18 and the remainder of the upper loader body 2a. In other embodiments, the proximal upper spring 18 may be connected to a remainder of the upper loader body 2a by a living hinge, which is a segment of material having lesser thickness that concentrates bending in that segment. Such a living hinge may be located at the junction between the proximal upper spring 18 and the remainder of the upper loader body 2a.

The upper surface of the proximal upper spring 18 may have any suitable shape. Referring to FIG. 4, at least a portion of the lower surface 24 of the proximal upper spring 18 may be angled downward proximally from the junction between the distal end 22 of the proximal upper spring 18 and the remainder of the upper loader body 2a. At least a portion of the lower surface 24 may be substantially planar. In other embodiments, at least a portion of the lower surface 24 of the proximal upper spring 18 may be curved, or otherwise shaped, downward proximally from the junction between the distal end 22 of the proximal upper spring 18 and the remainder of the upper loader body 2a. The proximal upper spring 18 may include a proximal fin 26 at its proximal end. The proximal fin 26 includes the lowest point on the proximal upper spring 18. Viewed from the side, the bottom 28 of the proximal fin 16 may be generally V-shaped, or may be shaped in any other suitable manner that facilitates engagement between the proximal fin 16 and the cartridge 4.

The proximal upper spring 18 may be tapered laterally in the proximal and/or downward directions; for example, as shown in FIG. 4. The proximal upper spring 18 may have any suitable cross-section perpendicular to the longitudinal axis of the loader 2 that allows it to engage the trough 12 and/or other portion of the cartridge 4 effectively. For example, where the trough 12 is substantially V-shaped and/or tapered in the downward direction, the cross-section perpendicular to the longitudinal axis of the loader 2 of the proximal upper spring 18 similarly may be substantially V-shaped and/or tapered in the downward direction.

As shown in FIGS. 1-5, the proximal upper spring 18 is in a neutral position. In the neutral position, the proximal upper spring 18 and/or its junction with the remainder of the upper loader body 2a does not store potential energy resulting from flexure of the proximal upper spring 18. The proximal upper spring 18 may be fabricated at the same time as the remainder of the upper loader body 2a, may be fabricated by cutting the slots 20 in the upper loader body 2a after fabrication of that component, or in any other suitable manner.

Figure 6:
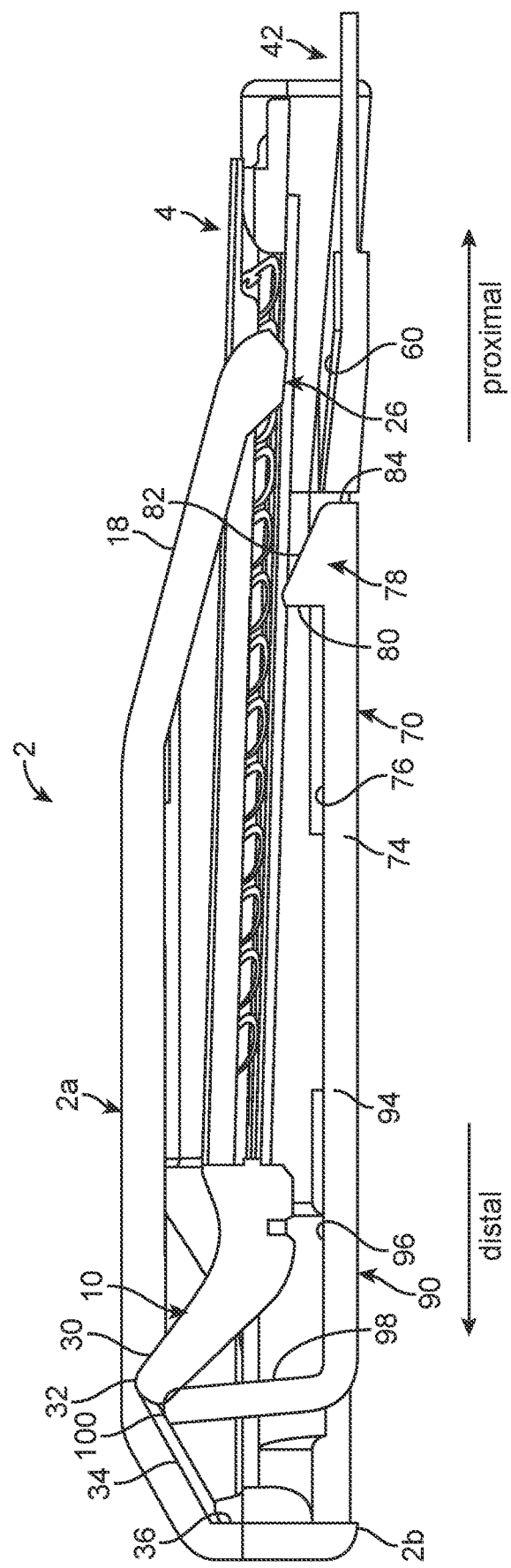
FIG. 6 is a side cross-section view of the exemplary loader with a cartridge held thereby of FIG. 2.

Referring also to FIG. 6, the distal end of the inner surface 16 of the upper loader body 2a is shaped to assist in holding the cartridge 4 in place in the loader 2. In the inner surface 16, a retainer ramp 30 extends upward in the distal direction. The retainer ramp 30 may be substantially flat, as seen in FIG. 6, or may be curved or shaped in any other suitable manner. As described in greater detail below, initially the distal end of the curved tip 10 is positioned distal to and in contact with the retainer ramp 30. Distal to the retainer ramp 30, the inner surface 16 curves substantially at a peak 32 to match the curvature of the distal end of the curved tip 10. In other embodiments, the inner surface 16 is shaped in any other suitable manner that accommodates the distal end of the curved tip 10. Distal to the peak 32, a seating ramp 34 extends downward in the distal direction. The seating ramp 34 may be substantially flat, as seen in FIG. 6, or may be curved or shaped in any other suitable manner. The seating ramp 34 may be angled downward at substantially a 30 degree angle to a horizontal plane, or may be angled or oriented in any other suitable manner. At the distal end of the seating ramp 34, optionally a wall 36 may extend downward substantially vertically. The retainer ramp 30, peak 32, and/or seating ramp 34 may have any suitable width; one or more may be as wide as the distal end of the curved tip 10, narrower than the distal end of the curved tip 10, or wider than the distal end of the curved tip 10.

Figure 7:
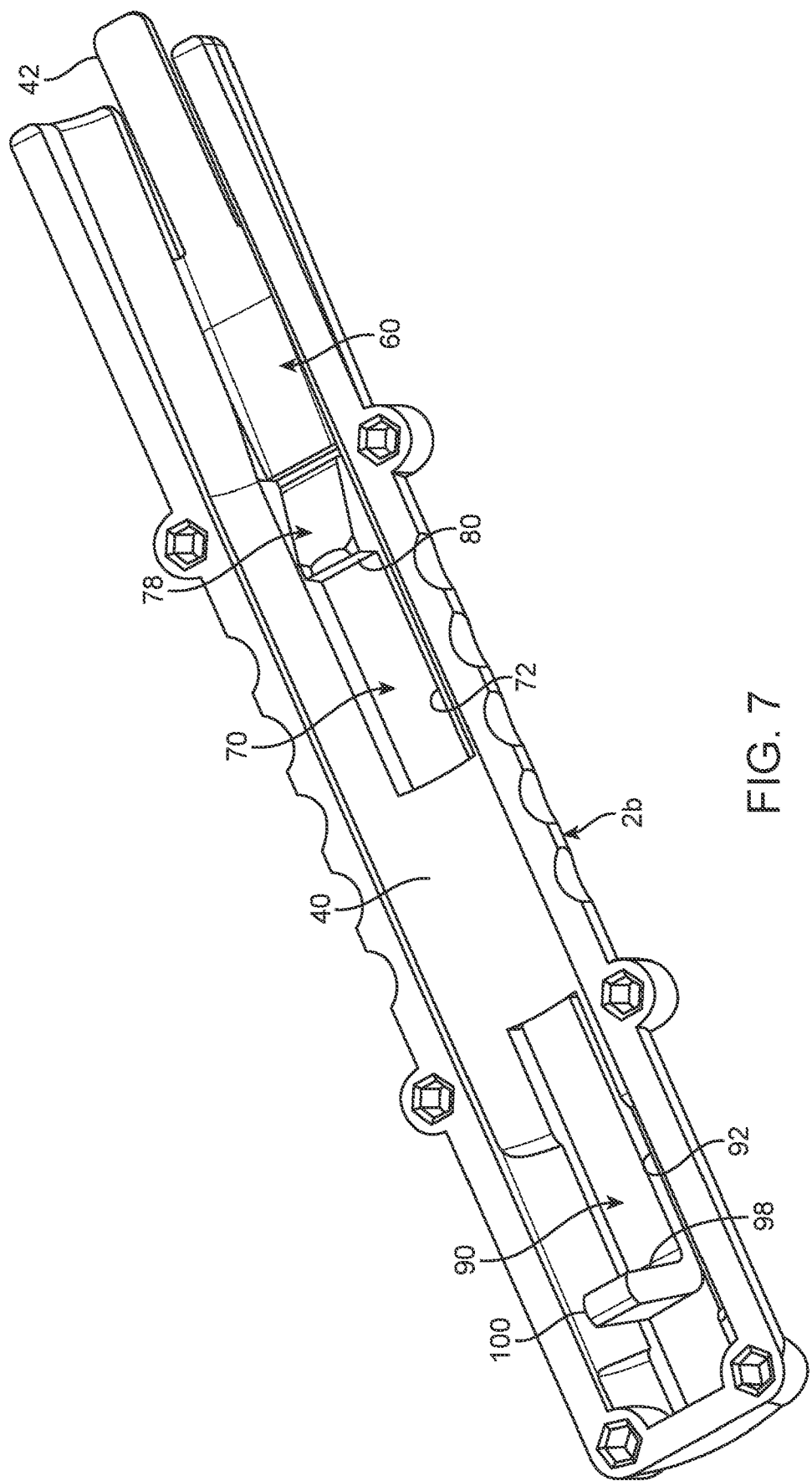
FIG. 7 is a perspective view into a lower loader body of the loader of FIG. 1.
Figure 8:
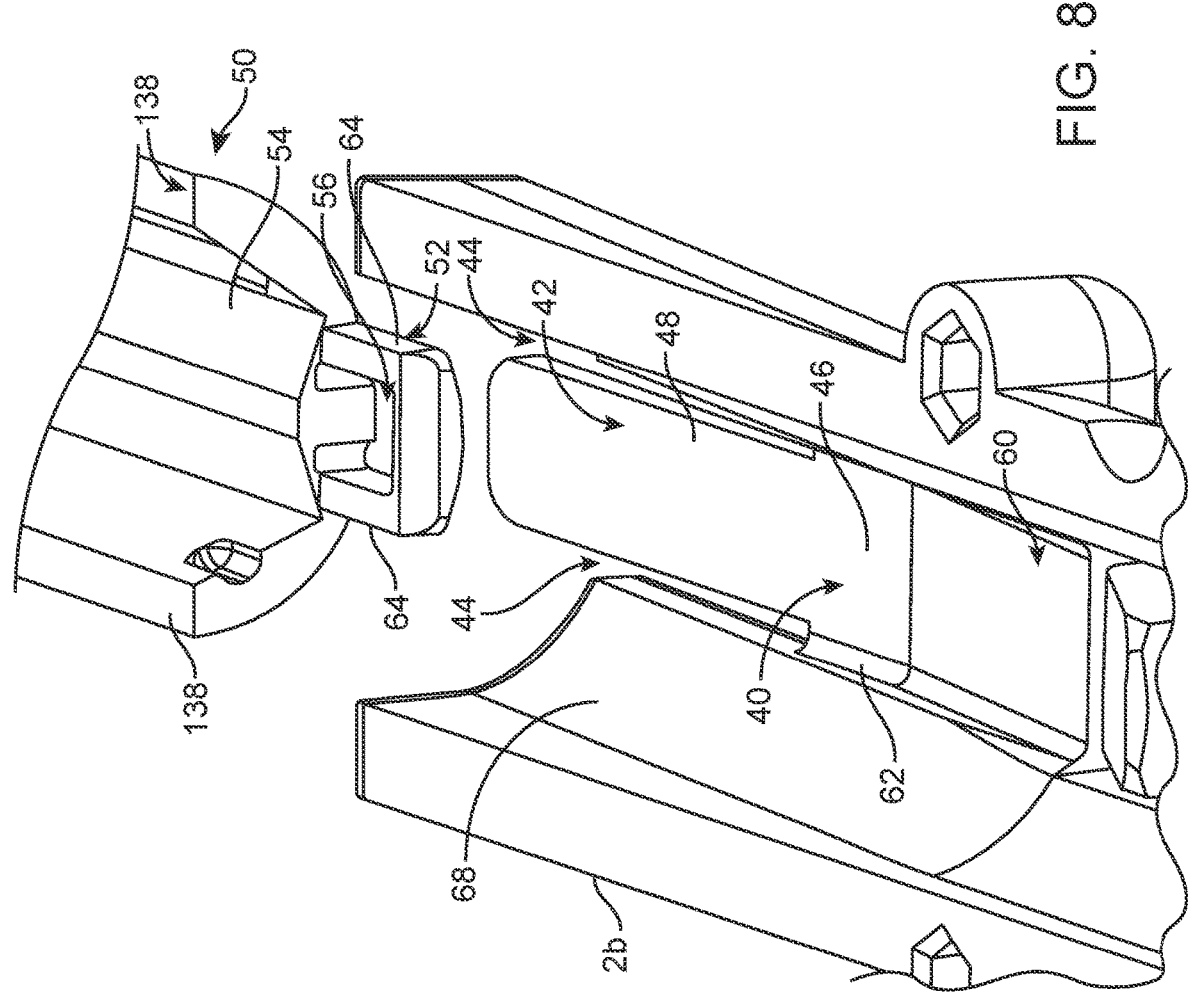
FIG. 8 is a perspective view of the proximal end of the exemplary loader of FIG. 1 and an exemplary stapler channel in proximity to one another.

Referring also to FIG. 7, an inner surface 40 of the lower loader body 2b defines part of the cavity 14 described above. Referring also to FIG. 8, a tongue 42 extends proximally from a remainder of the lower loader body 2b. Slots 44 may extend laterally along the lateral sides of the tongue 42, separating the lateral sides of the tongue 42 from a remainder of the lower loader body 2b. The distal end 46 of the tongue 42 may be connected to a remainder of the lower loader body 2b in any suitable manner. In one embodiment, the distal end 46 of the tongue 42 has the same thickness as the adjacent portion of the lower loader body 2b. In other embodiments, the tongue 42 may be connected to a remainder of the lower loader body 2b by a living hinge, which is a segment of material having lesser thickness that concentrates bending in that segment. Such a living hinge may be located at the junction between the tongue 42 and the remainder of the lower loader body 2b. The upper surface 48 of the tongue 42 may be substantially flat, or may have any other suitable shape. The lower surface of the tongue 42 may have any suitable shape. As seen in FIG. 6, the tongue 42 may have a substantially constant thickness along its longitudinal dimension. Alternately, in other embodiments the tongue 42 may vary in thickness along at least part of its length.

Referring to FIG. 8, a stapler channel 50 is shown. The stapler channel 50 is the portion of the end effector of a surgical stapler that is configured to receive the cartridge 4. The stapler channel 50 and the bottom of the cartridge 4 may have any suitable shapes as long as they are able to mate and the stapler channel 50 is able to hold the cartridge securely. For example, as shown in FIG. 8, the inner surface stapler channel 50 forms a generalized "W" shape. A channel boss 52 extends from the distal end of the stapler channel 50. Advantageously, the channel boss 52 extends from the bottom of the stapler channel 50. In one embodiment, the channel boss 52 includes a generally square channel boss opening 56 defined therethrough. In other embodiments, the channel boss opening need not extend all the way through the channel boss 52. In other embodiments, the channel boss opening 56 may have any other suitable shape, such as but not limited to rectangular, circular or oval. The channel boss opening 56 has a size and shape suitable to engage a cartridge bump, as described in greater detail below.

Returning to the loader 2 and referring also to FIGS. 1, 3 and 6-8, a ramp 60 extends upward in the distal direction from the distal end of the tongue 42. The ramp 60 is sized and shaped to engage the channel boss 52 upon loading, as described in greater detail below. In one embodiment, the ramp 60 is substantially as wide as the channel boss 52. Optionally, on the inner surface 40 of the lower loader body 2b, two keying walls 62 may be provided, each spaced apart from the tongue 42 by a corresponding slot 44. The keying walls 62 engage the sides 64 of the channel boss 52 to ensure proper orientation of the stapler channel 50 relative to the loader 2 and cartridge 4 during loading, as described in greater detail below. To both sides of the ramp 60, walls 68 are defined on the inner surface 40 of the lower loader body 2b, where the walls 68 have a shape and size corresponding to the outer shape and size of the stapler channel 50.

Referring also to FIGS. 3, 6 and 7, a proximal bottom spring 70 extends proximally from a remainder of the lower loader body 2b. Slots 72 may extend laterally along the lateral sides of the proximal bottom spring 70, separating the lateral sides of the proximal bottom spring 70 from a remainder of the lower loader body 2b. The distal end 74 of the proximal bottom spring 70 may be connected to a remainder of the lower loader body 2b in any suitable manner. In one embodiment, the proximal bottom spring 70 has the same thickness as the adjacent portion of the lower loader body 2b and extends proximally from the junction between the distal end 74 of the proximal bottom spring 70 and the remainder of the lower loader body 2b. In other embodiments, the proximal bottom spring 70 may be connected to a remainder of the lower loader body 2b by a living hinge, which is a segment of material having lesser thickness that concentrates bending in that segment. Such a living hinge may be located at the junction between the proximal bottom spring 70 and the remainder of the lower loader body 2b.

The lower surface of the proximal bottom spring 70 may have any suitable shape. Referring to FIG. 6, at least a portion of the upper surface 76 of the proximal bottom spring 70 may be substantially planar from the junction between the distal end 74 of the proximal bottom spring 70 and the remainder of the lower loader body 2b. That planar portion of the upper surface 76 may be substantially parallel to the longitudinal centerline of the loader 2. In other embodiments, at least a portion of the upper surface 76 of the proximal bottom spring 70 may be curved, or otherwise shaped, proximally from the junction between the distal end 74 of the proximal bottom spring 70 and the remainder of the lower loader body 2b.

The proximal bottom spring 70 may include a tab 78 at its proximal end. The tab 78 may include a distal surface 80 that is substantially perpendicular to the planar upper surface 76 of the proximal bottom spring 70. The distal surface 80 may be substantially planar. In other embodiments, the distal surface 80 may be oriented and/or shaped in any other suitable manner. The tab 78 may include an upper tab surface 82 that is angled downward in the proximal direction from its junction with the distal surface 80. The upper tab surface 82 may be substantially planar. In other embodiments, the upper tab surface 82 may be curved or may be shaped in any other suitable manner. At its proximal end, the upper tab surface 82 intersects a proximal surface 84 of the tab 78. The intersection between the upper tab surface 82 and proximal surface may be curved, or may be an angle or any other suitable shape. The proximal surface 84 may be substantially planar. In other embodiments, the proximal surface 84 may be curved or may be shaped in any other suitable manner.

As shown in FIGS. 1-6, the proximal bottom spring 70 is in a neutral position. In the neutral position, the proximal bottom spring 70 and/or its junction with the remainder of the lower loader body 2b does not store potential energy resulting from flexure of the proximal bottom spring 70. The proximal bottom spring 70 may be fabricated at the same time as the remainder of the lower loader body 2b, may be fabricated by cutting the slots 20 in the lower loader body 2b after fabrication of that component, or in any other suitable manner. The proximal bottom spring 70 and proximal upper spring 18 each may be in the neutral position prior to loading. When the loader 2 holds a cartridge 4, the shapes of the proximal bottom spring 70 and proximal upper spring 18 interact with the cartridge 4 to maintain a gap between the cartridge 4 and the inner surface 40 of the lower loader body 2b. Thus, when the loader 2 holds a cartridge 4, at least one of the proximal bottom spring 70 and proximal upper spring 18 may be deflected away from a neutral position, such that at least one of the proximal bottom spring 70 and proximal upper spring 18 is biased against the cartridge 4 to hold the cartridge 4 securely in place.

The upper tab surface 82 of the proximal bottom spring 70 contacts a portion of the cartridge 4. As seen in FIG. 6, the upper tab surface 82 contacts the cartridge 4 at a location distal to the point of contact between the proximal upper spring 18 and the cartridge 4. The proximal bottom spring 70 exerts more force upward on the cartridge 4 than the proximal upper spring 18 exerts downward on the cartridge 4 during insertion, as described in greater detail below. In this way, as in the neutral position, the proximal bottom spring 70 and proximal upper spring 18 advantageously interact to maintain a gap between the cartridge 4 and the inner surface 40 of the lower loader body 2b.

Referring also to FIGS. 3, 6 and 7, a distal bottom spring 90 extends distally from a remainder of the lower loader body 2b. Slots 92 may extend laterally along the lateral sides of the distal bottom spring 90, separating the lateral sides of the distal bottom spring 90 from a remainder of the lower loader body 2b. The proximal end 94 of the distal bottom spring 90 may be connected to a remainder of the lower loader body 2b in any suitable manner. In one embodiment, the distal bottom spring 90 has the same thickness as the adjacent portion of the lower loader body 2b and extends distally from the junction between the proximal end 94 of the distal bottom spring 90 and the remainder of the lower loader body 2b. In other embodiments, the distal bottom spring 90 may be connected to a remainder of the lower loader body 2b by a living hinge, which is a segment of material having lesser thickness that concentrates bending in that segment. Such a living hinge may be located at the junction between the distal bottom spring 90 and the remainder of the lower loader body 2b.

The lower surface of the distal bottom spring 90 may have any suitable shape. Referring to FIG. 6, at least a portion of the upper surface 96 of the distal bottom spring 90 may be substantially planar from the junction between the proximal end 94 of the distal bottom spring 90 and the remainder of the lower loader body 2b. That planar portion of the upper surface 96 may be substantially parallel to the longitudinal centerline of the loader 2. In other embodiments, at least a portion of the upper surface 96 of the distal bottom spring 90 may be curved, or otherwise shaped, distally from the junction between the proximal end 94 of the distal bottom spring 90 and the remainder of the lower loader body 2b.

The distal bottom spring 90 may include a finger 98 at its distal end. The finger 98 extends upward from a remainder of the distal bottom spring 90, and may form an angle with the remainder of the distal bottom spring 90. The finger 98 may be angled distally relative to a remainder of the distal bottom spring 90, as seen in FIG. 6. The tip 100 of the finger 98 may be curved, rounded or otherwise smooth. In other embodiments, the tip 100 of the finger 98 may be angled or flat. The tip 100 of the finger 98 initially engages a portion of the curved tip 10 of the cartridge 4, as described in greater detail below. As shown in FIGS. 1-6, the distal bottom spring 90 is in a neutral position. In the neutral position, the distal bottom spring 90 and/or its junction with the remainder of the lower loader body 2b does not store potential energy resulting from flexure of the distal bottom spring 90. The distal bottom spring 90 may be fabricated at the same time as the remainder of the lower loader body 2b, may be fabricated by cutting the slots 92 in the lower loader body 2b after fabrication of that component, or in any other suitable manner. In the neutral position, the tip 100 of the finger 98 is not biased against the curved tip 10 of the cartridge 4, but rather rests against the curved tip 10 of the cartridge 4 to assist in holding the cartridge 4 in place. In other embodiments, when the loader 2 holds a cartridge 4, the distal bottom spring 90 may be deflected away from a neutral position, such that distal bottom spring 90 is biased against the cartridge 4 to hold the cartridge 4 securely in place.

The outer surface 110 may include one or more grooves 112 defined therein, in order to facilitate grasping of the loader 2 between fingers of a user. In other embodiments, the grooves 112 may be omitted. The surface finish of the loader 2 advantageously facilitates the ability of a user to grasp and hold the loader 2. In other embodiments, the user grasps the loader 2 with a forceps or other instrument in use, such that the surface finish of the loader 2 is not as important to its function.

Unloader

Figure 9:
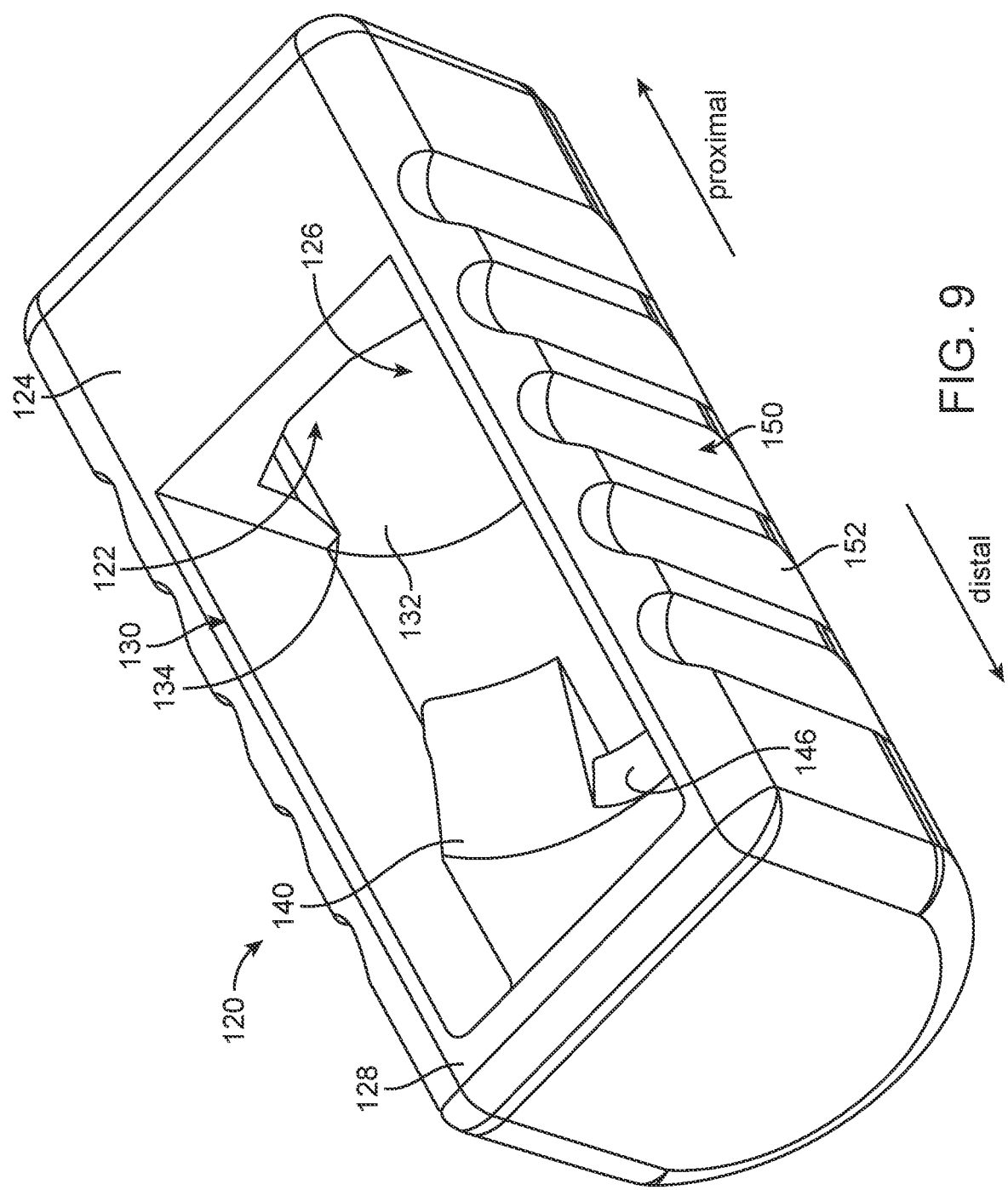
FIG. 9 is a perspective view of an exemplary unloader.
Figure 10:
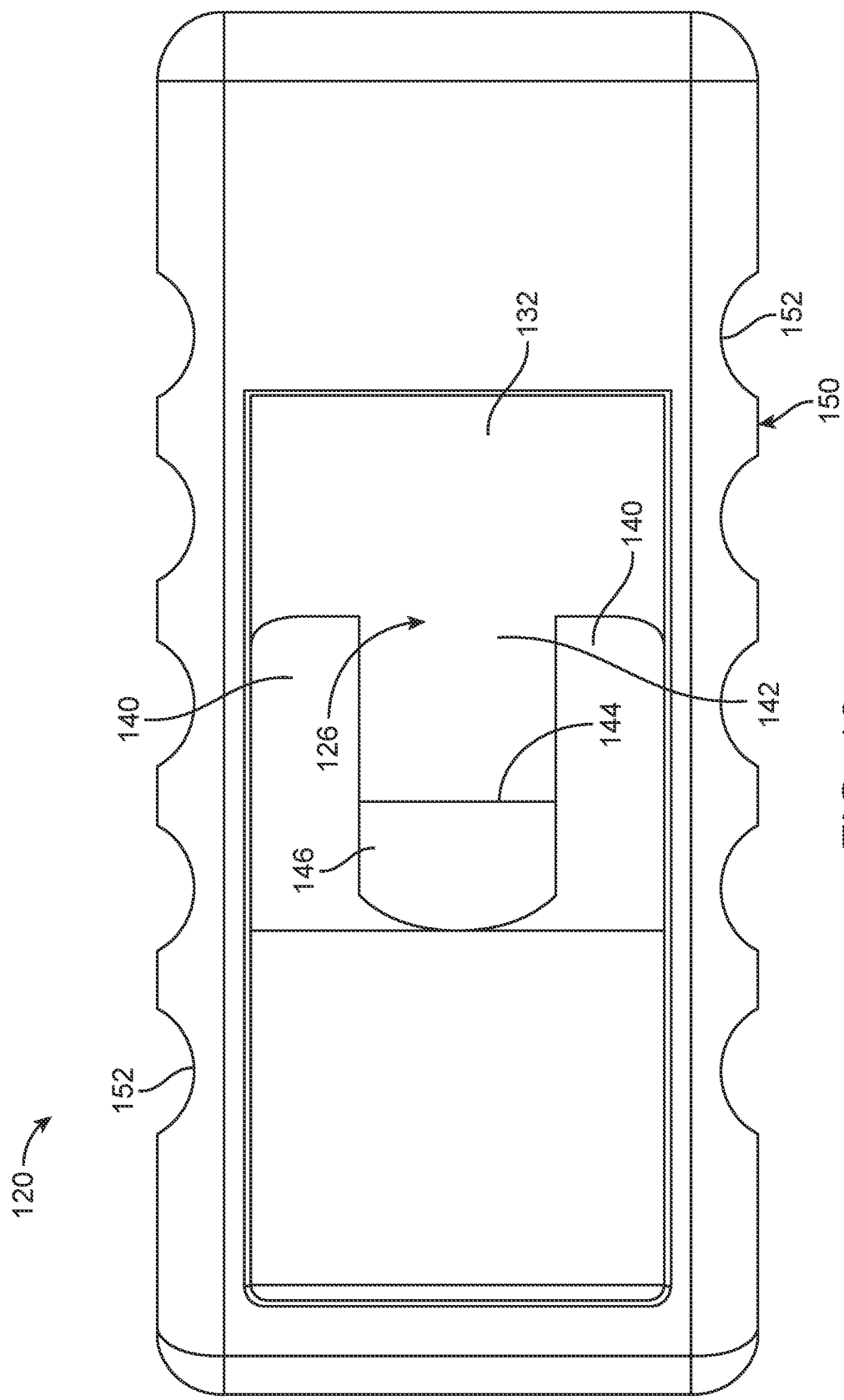
FIG. 10 is a top view of the unloader of FIG. 9.
Figure 11:
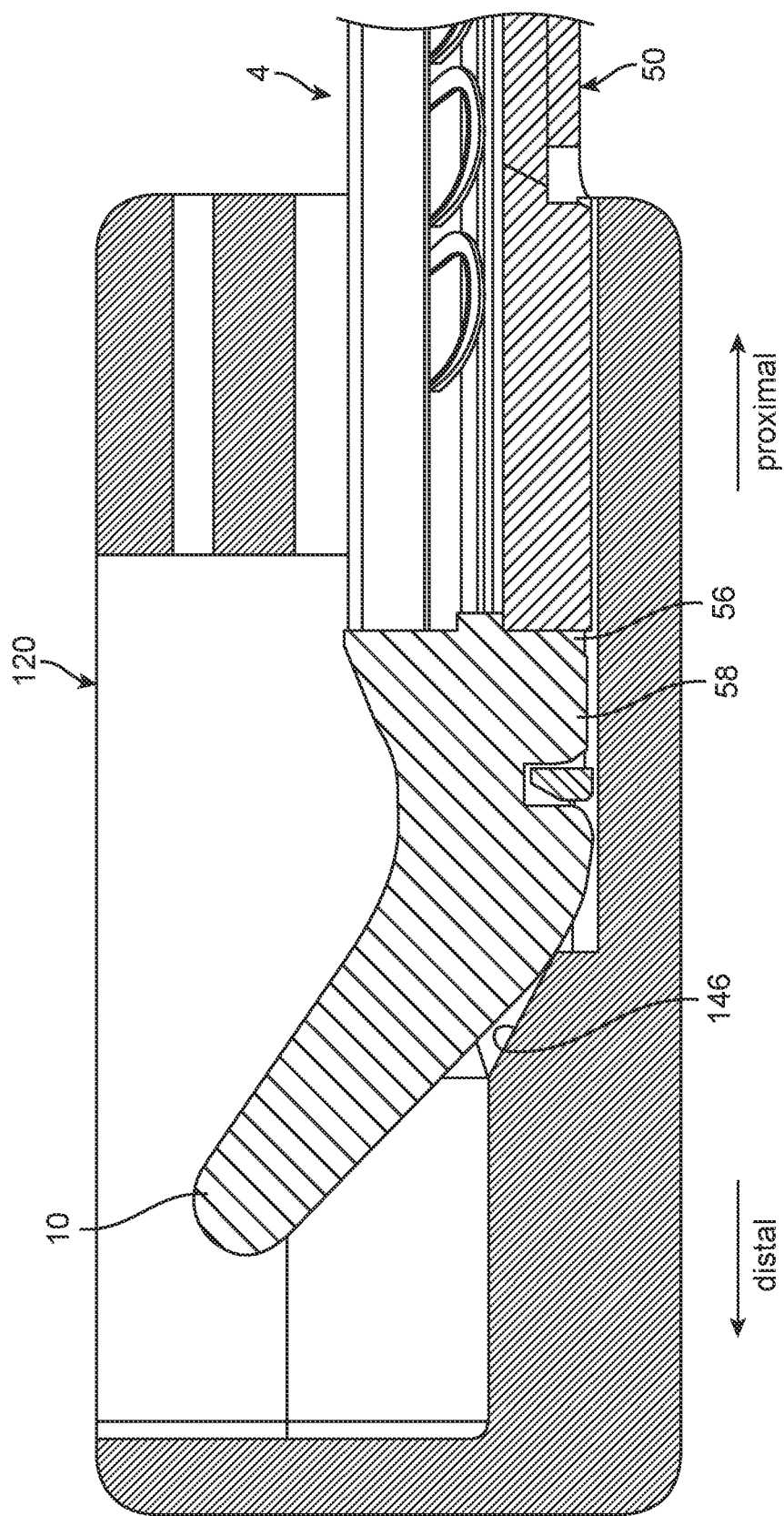
FIG. 11 is a side cross-section view of a curved-tip cartridge engaged with a channel boss of the stapler channel.
Figure 12:
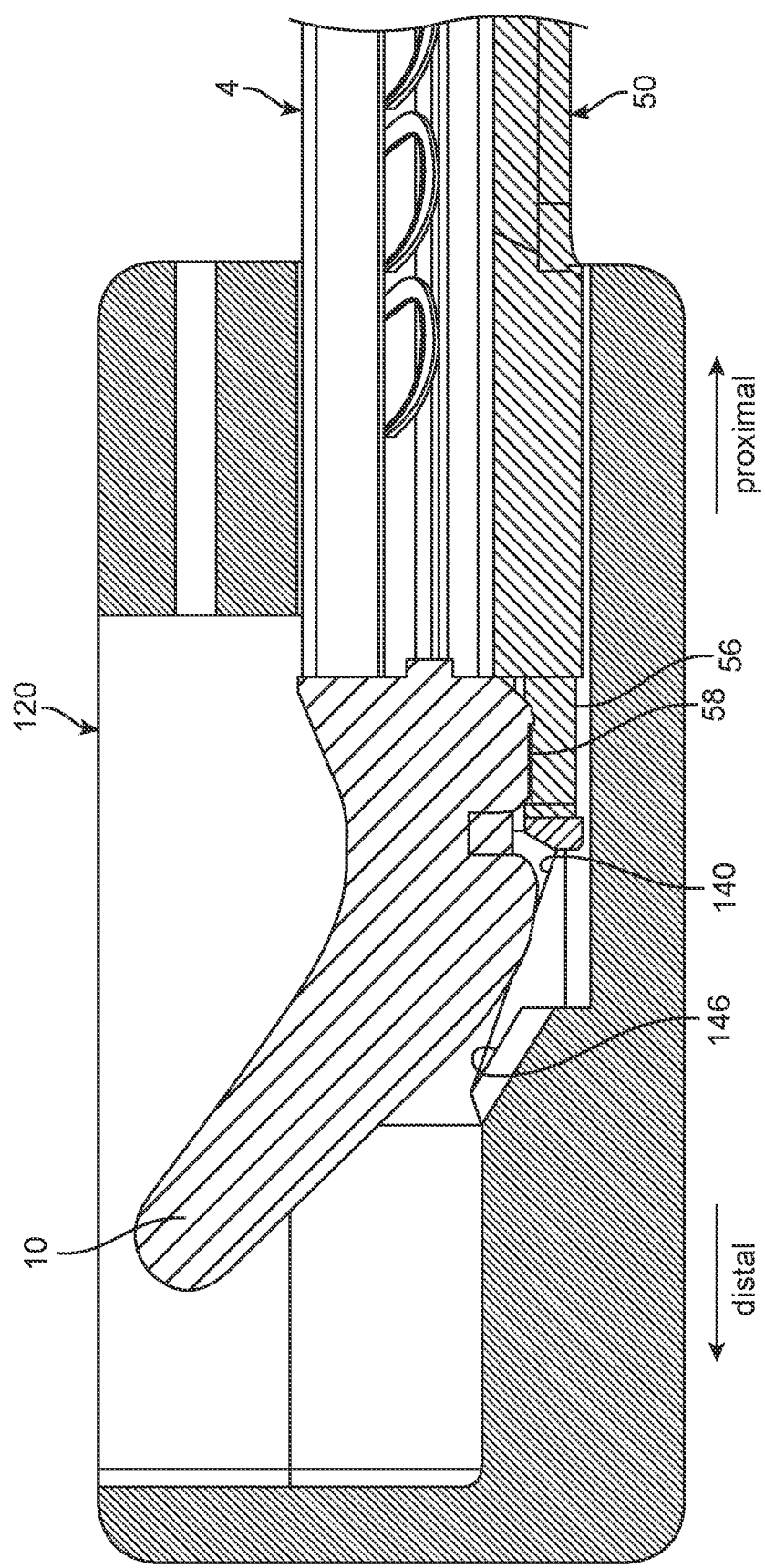
FIG. 12 is a side cross-section view of the unloader of FIG. 9, disengaging a curved-tip cartridge from a stapler channel.
Figure 13:
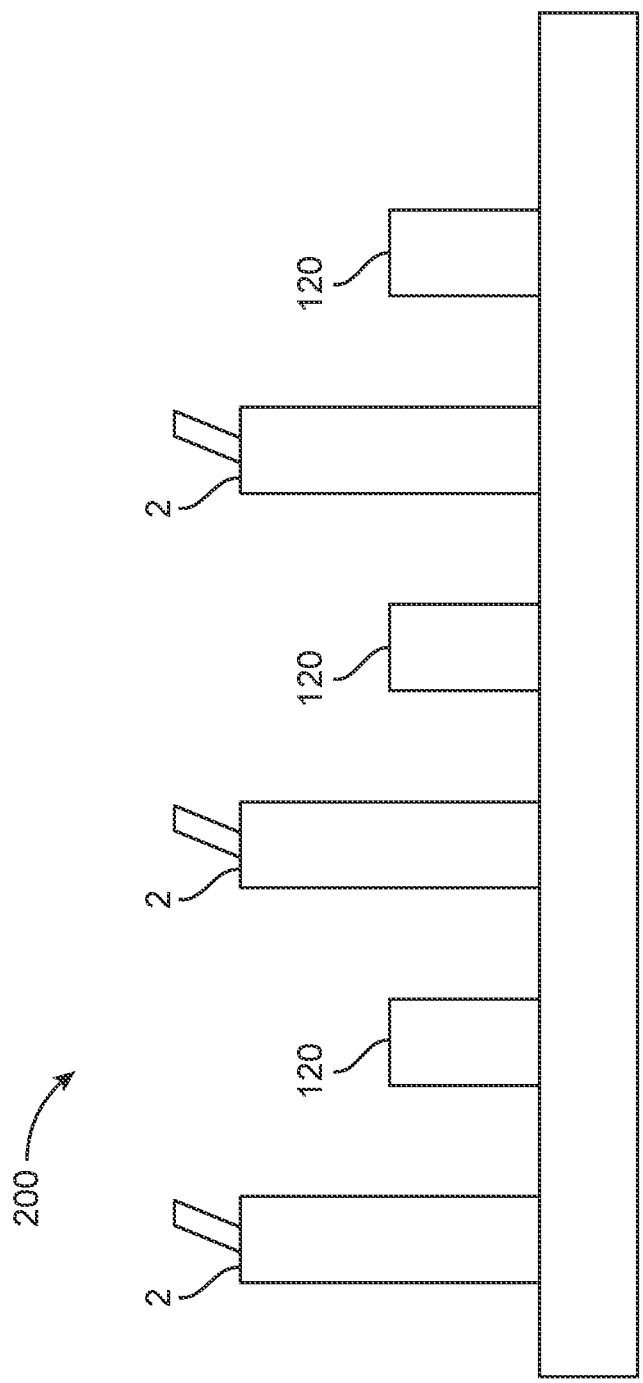
FIG. 13 is a schematic drawing of a magazine including a plurality of loaders and unloaders.

Referring to FIGS. 9-11, an unloader 120 is shown. The unloader 120 provides an ergonomic and simple way to remove a curved-tip cartridge 4 from a stapler channel 50. The unloader 120 may be fabricated as a one-piece component, such as by injection molding, additive manufacturing (colloquially referred to as "3-D printing"), by stamping, or by any other suitable process. Alternately, two or more components may be fabricated separated and then later assembled in any suitable manner to form the unloader 120.

The unloader 120 may include an aperture 122 defined through its proximal end. The aperture 122 extends through a proximal body 124 of the unloader 120. The interior of the unloader 120 may be a cavity 126. The upper surface 128 of the unloader 120 may include an opening 130 defined therethrough. The upper surface 128 of the unloader 120 may be generally planar. Alternately, the upper surface 128 of the unloader 120 may have any other suitable shape. The size and shape of the opening 130 is defined by the intersection between the cavity 126 and the upper surface 128 of the unloader 120. In some embodiments, the opening 130 may be substantially rectangular. In another embodiments, the opening 130 may have any other shape and/or symmetry, or may be asymmetrical in configuration.

The shape of at least part of the perimeter of the aperture 122 and/or of a lower surface 132 of the cavity 126 may correspond to the shape and size of the stapler channel 50. As described in greater detail below, as part of the unloading process the stapler channel 50 may be slid through and held by the aperture 122, such that the shapes of the aperture 122 and stapler channel 50 are related. In one embodiment, the aperture 122 includes a horizontal plane 134 on each lateral side, such that the horizontal planes 134 are spaced laterally apart from one another on opposite sides of the perimeter of the aperture 122. Referring also to FIG. 8, each horizontal plane 134 is configured to engage a corresponding upper edge 138 of the stapler channel 50. This engagement assists in holding the stapler channel 50 securely relative to the unloader 120 during the unloading process, and also provides a keying element to ensure the stapler channel 50 is inserted correctly into the unloader 120. The bottom edge of the aperture 122 may be defined by the lower surface 132 of the cavity 126 of the unloader 120. The lower surface 132 of the cavity 126 may be curved in a generally concave manner. The size and shape of the lower surface 132 and the horizontal planes 134 may be toleranced relative to the stapler channel 50 to both allow the stapler channel 50 to slide through the aperture 122, and to hold the stapler channel 50 in a desired position relative to the unloader 120.

Referring to FIGS. 9-10, two side ramps 140 are spaced distally from the aperture 122 and are spaced laterally apart from one another. Each side ramp 140 extends upward in the distal direction from the lower surface 132 of the cavity 126. Longitudinally between the side ramps 140 and the aperture 122, the curvature of the lower surface 132 is substantially constant. The side ramps 140 are laterally spaced from one another a distance substantially equal to the width of the channel boss 52. The space between the side ramps 140 may be referred to as the trough 142. At the distal end of the trough 142 is a stop 144, which is configured to contact the end of the channel boss 52 and thereby stop longitudinal relative motion between the stapler channel 50 and the unloader 120. The stop 144 provides a hard stop to enhance control and to enhance control and to provide feedback to the user that the stapler channel 50 has moved sufficiently far to unload the cartridge 4. The stop 144 may be a vertical wall extending upward from the lower surface 132 of the cavity 126. In some embodiments, the stop 144 is substantially as tall as the channel boss 52. In other embodiments, the stop 144 may be taller or shorter than the channel boss 52.

A center ramp 146 extends upward in the distal direction from the top of the stop 144. The center ramp 146 may be substantially planar. In other embodiments, the center ramp 146 may be curved, or may be shaped in any other suitable manner. As described in greater detail below, the center ramp 146 is configured to engage the curved tip cartridge 4 as the unloader 120 and stapler channel 50 move relatively toward one another.

The outer surface 150 may include one or more grooves 152 defined therein, in order to facilitate grasping of the unloader 120 between fingers of a user. In other embodiments, the grooves 152 may be omitted. The surface finish of the unloader 120 advantageously facilitates the ability of a user to grasp and hold the unloader 120. In other embodiments, the user grasps the unloader 120 with a forceps or other instrument in use, such that the surface finish of the unloader 120 is not as important to its function.

Operation—Loader

For the purpose of this description, initially, a fresh, unused cartridge 4 is held by the loader 2, and the stapler channel 50 is empty and does not hold a cartridge.

The user grasps the loader 2 that holds a fresh cartridge 4, with his or her fingers, forceps, grasper, robotic end effector, or other tool. The user may be a physician or may be a person who is performing tests on the loader 2 and/or cartridge 4, such as quality control testing during manufacturing. As used in this document, the term "possessing" the loader 2 means affirmatively holding the loader 2 directly with a hand or indirectly via an intervening tool or tools.

Initially, referring also to FIGS. 4 and 6, the loader 2 holds the cartridge 4 securely. The proximal bottom spring 70 exerts an upward force on the cartridge 4, such as via contact between the tab 78 of the proximal bottom spring 70 and the bottom of the cartridge 4. The presence of the cartridge 4 in the loader 2 deflects the proximal bottom spring 70 downward, such that the proximal bottom spring 70 stores energy and is biased upward against the cartridge 4. The proximal upper spring 18 exerts a downward force on the cartridge 4, such as via contact between the proximal fin 26 of the proximal upper spring 18 and the top of the cartridge 4.

According to some embodiments, the force exerted upward by the proximal bottom spring 70 on the cartridge 4 is greater than the force exerted downward by the proximal upper spring 18 on the cartridge. Further, according to some embodiments, the location of contact between the proximal bottom spring 70 and the cartridge 4 is distal to the location of contact between the proximal upper spring 18 and the cartridge 4. As a result, the proximal upper spring 18 and proximal bottom spring 70 maintain a gap between the cartridge 4 and the inner surface 40 of the lower loader body 2b. Further, the engagement between the proximal upper spring 18, proximal bottom spring 70, and the cartridge 4 assists in orienting the distal end of the cartridge 4 upward, due to the difference in longitudinal location of contact with the cartridge 4 of the proximal upper spring 18 and the proximal bottom spring 70. Initially, in some embodiments, prior to loading, the distal end of the curved tip 10 rests against the peak 32 in the inner surface 16 of the upper loader body 2a. Further, the tip 100 of the finger 98 of the distal bottom spring 90 may be biased upward against the curved tip 10.

Next, the user causes at least one of the loader 2 and the stapler channel 50 to move toward the other, in any suitable manner. As a result of that moving, the stapler channel 50 engages the loader 2. In one embodiment, referring also to FIGS. 6-8, the distal end of the stapler channel 50 engages the tongue 42, deflecting the tongue 42 downward. As described above, the stapler channel 50 optionally includes a channel boss 52 at a distal end thereof. The channel boss 52 slides between the two keying walls 62 defined in the inner surface 40 of the lower loader body 2b. Engagement between the keying walls 62 and the lateral sides 64 of the channel boss 52 provides rotational alignment between the cartridge 4 and the stapler channel 50, which allows the stapler channel 50 to receive the cartridge 4 properly. Alternately, one or more other keying features may be provided to align the loader 2 and stapler channel 50 relative to one another, whether or not the stapler channel 50 includes a channel boss 52. As the stapler channel 50 itself enters the loader 2, the stapler channel 50 is received by the walls 68 defined on the inner surface 40 of the lower loader body 2b, which correspond to the shape of the stapler channel 50, and which may be dimensioned to be slightly larger than the corresponding dimensions of the stapler channel 50. The walls 68 act as secondary keying fixtures to hold the stapler channel 50 in a desired rotational alignment.

As the loader 2 and stapler channel 50 continue to slide together, the channel boss 52 slides up the ramp 60 defined in the inner surface 40 of the lower loader body 2b. As sliding continues, the channel boss 52 slides off the distal end of the ramp 60 and into engagement with the upper tab surface 82 of the tab 78. The upper tab surface 82 is angled downward in the proximal direction, and the proximal end of the upper tab surface 82 may be in proximity to the ramp 60. Thus, as the channel boss 52 slides distal to the distal end of the ramp 60, it slides along the upper tab surface 82 of the tab 78. As the channel boss 52, followed by a remainder of the stapler channel 50, slides against the upper tab surface 82, the channel boss 52 and then the stapler channel 50 urge the tab 78 downward.

Motion of the tab 78 downward by its contact with the channel boss 52 and then the stapler channel 50 causes the tab 78, and the proximal bottom spring 70, to move out of engagement with the cartridge 4. As described above, the proximal bottom spring 70 initially exerts a force upward on the cartridge 4 that is greater than the force exerted downward by the proximal upper spring 18 on the cartridge. By disengaging the proximal bottom spring 70 from the cartridge 4, the channel boss 52 and then the stapler channel 50 remove from the cartridge 4 the upward force applied to the cartridge 4 by the proximal bottom spring 70. As a result, the downward force applied to the cartridge 4 by the proximal upper spring 18 is counteracted no longer by the proximal bottom spring 70, and the proximal upper spring 18 pushes the cartridge 4 downward into the stapler channel 50 such as via contact between the proximal fin 26 of the proximal upper spring 18 and the top of the cartridge 4. At the same time, due to the contact between the ramp 60 and stapler channel 50 that urges the stapler channel 50 upward relative to the proximal upper spring 70, the stapler channel 50 is pushed upward relative to the cartridge 4.

The cartridge 4 begins to seat in the stapler channel 50. Due to contact between the tip 100 of the finger 98 of the distal bottom spring 90 and the distal end of the cartridge 4, the distal end of the cartridge 4 remains higher than the proximal end of the cartridge 4. Such an orientation of the cartridge 4 allows the proximal end of the cartridge 4 to seat first in the stapler channel 50, before the distal end of the cartridge 4. In some embodiments, it may be advantageous to seat the proximal end of the cartridge 4 in the stapler channel 50 before a remainder of the cartridge 4, due to locking mechanisms or other structural or mechanical interconnections that may be made between the proximal end of the cartridge 4 and one or more elements of or associated with the stapler channel 50. Alternately, the proximal end of the cartridge 4 need not be seated first in the stapler channel 50, if desired.

As the loader 2 and stapler channel 50 continue to slide together, and the cartridge 4 begins to seat in the stapler channel 50, the linear component of relative motion between the loader 2 and the stapler channel 50 pushes the cartridge 4 distally in the loader 2. Referring also to FIG. 6, and as described above, initially the distal end of the curved tip 10 of the cartridge 4 resides against or in proximity to the peak 32 defined in the inner surface 16 of the upper loader body 2a. As the cartridge 4 is pushed distally in the loader 2, the distal end of the curved tip 10 of the cartridge 4 is pushed distally away from the peak 32 and onto the seating ramp 34 defined in the inner surface 16 of the upper loader body 2a distal to the peak 32. As described above, the seating ramp 34 extends downward in the distal direction from the peak 32. As the cartridge 4 is pushed distally in the loader 2, the distal end of the curved tip 10 of the cartridge 4 rides along the seating ramp 34. The interaction between the distal end of the curved tip 10 of the cartridge 4 and the seating ramp 34 urges the distal end of the cartridge 4 downward. This downward motion of the distal end of the curved tip 10 of the cartridge 4 pushes the finger 98 of the distal bottom spring 90 downward; the upward force exerted by the distal bottom spring 90 of the cartridge 4 is designed to be less than the downward force exerted by the downward motion of the distal end of the curved tip 10 of the cartridge 4.

Distal motion of the cartridge 4 ceases when the distal end of the curved tip 10 of the cartridge 4 encounters the wall 36 defined in the inner surface 16 of the upper loader body 2a. At or prior to the encounter between the distal end of the curved tip 10 of the cartridge 4 and the wall 36, the cartridge 4 seats completely in the stapler channel 50. Advantageously, this seating affirmatively connects the cartridge 4 to the stapler channel 50. In one embodiment, referring also to FIG. 11, a cartridge bump 58 engages the channel boss opening 56 of the channel boss 52 of the stapler channel 50, such as via a pressure fit. Optionally, this engagement may be confirmed audibly. For example, the cartridge bump 58 snaps into the channel boss opening 56, providing an audible snap that the user can hear, and audibly confirming the affirmative connection between the cartridge 4 and the stapler channel 50. To be clear, FIG. 11 shows the cartridge 4 and stapler channel 50 inside the unloader 120; however, the engagement between the cartridge bump 58 and the channel boss opening 56 as shown in FIG. 11 is the same as the engagement between the cartridge bump 58 and the channel boss opening 56 that results from the operation of the loader 2 described in this paragraph.

The cartridge 4 is now engaged with the stapler channel 50. The user then causes at least one of the loader 2 and the stapler channel 50 to move away from the other, in any suitable manner. The user continues to grasp the loader 2 that holds a fresh cartridge 4, with his or her fingers, forceps, grasper, robotic end effector, or other tool. Because the cartridge 4 is engaged with the stapler channel 50, the components of the loader 2 no longer affect the position of the cartridge 4 relative to the stapler channel 50. As the cartridge 4 and stapler channel 50 are withdrawn from the loader 2, the cartridge 4 and stapler channel 50 move proximal to the finger 98 of the distal bottom spring 90, which then moves upward toward its neutral position. The curved tip 10 of the cartridge 4 contacts the underside of the proximal upper spring 18 as the cartridge 4 continues to move proximally within the loader 2. The contact between the curved tip 10 of the cartridge 4 and the underside of the proximal upper spring 18 urges the proximal upper spring upward, out of the way of the cartridge 4 as it is withdrawn from the loader 2. As the curved tip 10 of the cartridge 4 moves proximal to the proximal upper spring 18, the cartridge 4 and stapler channel 50 are free from the loader 2, and the proximal upper spring 18 moves downward toward its neutral position.

The cartridge 4 is now loaded into the stapler channel 50 and ready for use.

Next, the user positions the cartridge 4 and stapler channel 50 adjacent to tissue to be treated in the patient and clamps or otherwise secures the cartridge 4 against that tissue. The stapler channel 50 is part of a surgical stapler, which may have any configuration. Actuation of the surgical stapler may be performed in any suitable manner, such as but not limited to actuation as described in commonly-assigned U.S. Pat. No. 7,988,026. Actuation of the surgical stapler causes the cartridge 4 to deploy one or more staples into tissue to be treated. In some embodiments, a plurality of staples are deployed into tissue as a result of direct contact between at least one wedge in the surgical stapler and a plurality of staples, as described in commonly-assigned U.S. Pat. No. 7,988,026. In some embodiments, a plurality of staples are broken off from a carrier during deployment into tissue, as described in commonly-assigned U.S. Pat. No. 7,988,026. After actuation, if the stapler channel 50 and cartridge 4 have been clamped against tissue, they are unclamped from tissue.

Operation—Unloader

After the stapler has been actuated and a plurality of staples have been deployed into tissue from the cartridge 4, that cartridge 4 is spent and is not usable for additional firings. If the user wishes to deploy additional staples into tissue, the user first removes the spent cartridge 4 from the stapler channel 50.

Referring also to FIGS. 9-12, the unloader 120 may be used to remove the spent cartridge 4 from the stapler channel 50. To do so, the user causes at least one of the unloader 120 and the combination of the cartridge 4 and stapler channel 50 to move toward the other, in any suitable manner. The shape of at least part of the perimeter of the aperture 122 of the unloader 120 may be defined by the shape of the combination of the cartridge 4 seated in the stapler channel 50. The aperture 122 advantageously acts as a keying feature, in order to provide rotational alignment between the combination of the cartridge 4 and the stapler channel 50 on the one hand and the unloader 120 on the other. In this way, the unloader 120 controls the rotational alignment of the combination of the cartridge 4 and the stapler channel 50 on the one hand and the unloader 120 on the other when the combination of the cartridge 4 and the stapler channel 50 is received in the aperture 122.

The aperture 122 also constrains the motion of the stapler channel 50 to a substantially linear motion along or parallel to the longitudinal axis of the unloader 120. The horizontal planes 134 on the lateral sides of the aperture 122 advantageously are sized and located to engage an upper surface or surfaces of the stapler channel 50, lateral to the cartridge 4, thereby constraining the motion of the stapler channel 50. Motion of the stapler channel 50 in any direction perpendicular to the linear direction of insertion of the stapler channel 50 into the aperture 122 is thus substantially restrained.

As the unloader 2 and the combination of the cartridge 4 and stapler channel 50 continue to slide together, the stapler boss 52 then slides substantially linearly into the trough 142 between the side ramps 140. The side ramps 140 and troughs 142 are spaced apart from the aperture 122, such that the stapler boss 52 slides into the trough 142 at a time spaced apart from the time at which the combination of the cartridge 4 and stapler channel 50 slides through the distal plane of the aperture 122. As the stapler boss 52 slides into the trough 142, referring also to FIG. 12, the underside of the distal end 10 of the cartridge 4 engages the center ramp 146 at the distal end of and above the trough 142.

As the unloader 2 and the combination of the cartridge 4 and stapler channel 50 continue to slide together, the distal end 10 of the cartridge 4 may engage the side ramps 140. Because the side ramps 140 are angled or otherwise oriented upward toward the distal direction, motion of the distal end 10 of the cartridge 4 along the side ramps 140 applies a force with an upward component to the distal end 10 of the cartridge 4, and thus urges the distal end 10 of the cartridge 4 upward. As the cartridge 4 and stapler channel 50 move distally relative to the unloader 120, the underside of the distal end 10 of the cartridge 4 then slides along the center ramp 146. According to other embodiments, the distal end 10 of the cartridge 4 may engage the center ramp 146 before or substantially at the same time as it engages the side ramps 140. Because the center ramp 146 is angled or otherwise oriented upward toward the distal direction, motion of the distal end 10 of the cartridge 4 along the center ramp 146 applies a force with an upward component to the distal end 10 of the cartridge 4, and thus urges the distal end 10 of the cartridge 4 upward. At the same time, the stapler channel 50 is restrained against upward motion by the horizontal planes 134 of the aperture 122, as described above. Due to engagement between the cartridge 4 and the side ramps 140 and/or the center ramp 146, sufficient force is exerted on the cartridge 4 in the upward direction to separate the cartridge 4 from the stapler channel 50. In one embodiment, a cartridge bump 58 had been engaged with the channel boss opening 56 of the channel boss 52 of the stapler channel 50 as shown in FIG. 11, such as by a pressure fit, and is disengaged from the channel boss opening 56 upon separation of the cartridge 4 from the stapler channel 50. Optionally, this disengagement may be confirmed audibly. For example, the cartridge bump 58 unsnaps from the channel boss opening 56, providing an audible snap that the user can hear, audibly confirming the disconnection between the cartridge 4 and the stapler channel 50. Before or after disconnection, the distal end of the curved tip 10 of the cartridge 4 may slide through the aperture 130, which is provided to allow unrestricted upward motion of the distal end of the curved tip 10. Contact between the end of the channel boss 52 and the stop 144 stops longitudinal relative motion between the stapler channel 50 and the unloader 120, to enhance control and to provide feedback to the user that the stapler channel 50 has moved sufficiently far to unload the cartridge 4.

The user then causes at least one of the unloader 120 and the stapler channel 50 to move away from the other, in any suitable manner. In some embodiments, the stapler boss 52 slides under the cartridge bump 58, such that the cartridge 4 cannot be reconnected accidentally to the stapler channel 50 during proximal motion of the stapler channel 50 relative to the unloader 120. Because the distal end of the cartridge 4 has been separated from the stapler channel 50, the proximal motion of the stapler channel 50 causes the proximal end of the cartridge 4 to separate from the stapler channel 50. The spent cartridge 4 thus is disconnected from the stapler channel 50, and held by the unloader 120. The stapler channel 50 is empty once again.

The user, under most circumstances, unloads a spent cartridge 4 in order to reload the stapler channel 4 with a fresh, unused cartridge 4. The user may repeat the loading process described above, and utilize a loader 2 holding a fresh cartridge 4 to install that cartridge 4 in the stapler channel 50.

According to some embodiments, one or more loaders 2 and/or unloaders 120 may be affixed to or fabricated as part of a magazine. Such a magazine may include several loaders 2 and/or unloaders 120, spaced apart from one another and arranged linearly or in any other suitable manner. The magazine may be placed in the sterile field in proximity to the patient, or may be located elsewhere in the operating room. The magazine holds the loaders 2 and/or unloaders 120 securely so that the user can utilize the loaders 2 and/or unloaders 120 without the need to grasp them; they are held securely as part of the magazine. The magazine may be clamped to structure near the patient, may be weighted and stand alone, or otherwise may be configured to be used as a standalone device without needing to be held by a user during loading and/or unloading. The magazine may be particularly useful in robotic surgery, such as utilizing the da Vinci surgical robot of Intuitive Surgical of Sunnyvale, Calif., where the stapler channel 50 is part of a robotic end effector or held by a robotic end effector. By placing the loaders 2 and/or unloaders 120 in a magazine in proximity to the patient, the user (who typically sits at a control console separate from the patient) can load and/or unload the stapler channel 50 from the control console using the robot alone, without additional human intervention to load and/or unload the stapler channel 50.

Referring also to FIG. 14, according to some embodiments, at least one loader 2 may be connected to at least one unloader 120 to form a unitary structure. For example, the distal end of a loader 2 may be connected to the distal end of an unloader 120, as the distal end of each is described above. Such a combination loader/unloader 210 may be fabricated as two or more components that are assembled together, or may be fabricated as a single component such as by injection molding or 3D printing. A grasp fixture 220 may be provided on an outer surface of the loader/unloader 210, such as at the junction between the loader 2 and unloader 120. In other embodiments, the grasp fixture 220 may be provided at any other suitable location on the outer surface of the loader/unloader 210. The grasp fixture 220 may be a post or other structure extending outward from the loader/unloader 210. The cross-section of the grasp fixture 220 may be square, round, triangular, rectangular, or any other suitable shape; the cross-section of the grasp fixture 220 may be substantially constant along the grasp fixture 220 or may vary along the grasp fixture 220.

The grasp fixture 220 may be engaged by a grasper, forceps, robotic end effector, or other tool. The combination loader/unloader 210 with a grasp fixture 220 may be useful for minimally-invasive surgery, particularly robotic surgery. The combination loader/unloader 210 may be used substantially as described above, with variations as described here. The stapler channel 50 is loaded outside the body and inserted into the body through a first trocar, and the combination loader/unloader 210 is inserted into the body through a second trocar at a time before, during or after insertion of the stapler channel 50 through the first trocar. After deploying staples in tissue, the stapler channel 50 need not be withdrawn from the first trocar. Instead, the stapler channel 50 may engage the unloader component of the combination loader/unloader 210 inside the body cavity of the patient. The cartridge 4 is unloaded from the stapler channel 50 in the same manner described above. The combination loader/unloader 210 then may be rotated substantially 180 degrees about an axis defined by the grasp fixture 220, such as by rotating a robotic grasper that engages the grasp fixture 220. In this way, the empty stapler channel 50 can remain in substantially the same place for reloading, simplifying the process. The stapler channel 50 and loader component of the combination loader/unloader 210 are then caused to move together relative to one another, and a fresh cartridge 4 is loaded into the stapler channel 50 in the same manner described above. The combination loader/unloader 210 is then removed from the body cavity of the patient through the second trocar. Alternately, the combination loader/unloader 210 may be used outside the body rather than inside the body, in substantially the same manner as described with regard to the operation of the loader 2 and unloader 120 separately.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A loader engageable with a workpiece stapler channel and a workpiece curved-tip cartridge held by that stapler channel, the loader comprising:

a cavity defined within the loader, wherein at least a distal portion of the workpiece curved-tip cartridge is held within said cavity;

a proximal upper spring defined in an upper portion of the loader and extending downward into said cavity, said proximal upper spring biased downward against the workpiece curved-tip cartridge with a first force;

a proximal bottom spring defined in a lower portion of the loader and extending upward into said cavity, said proximal bottom spring biased upward against the workpiece curved-tip cartridge with a second force greater than said first force; and a distal bottom spring defined in the lower portion of the loader and extending upward into said cavity at a location distal to said proximal bottom spring, wherein said distal bottom spring engages a distal segment of the workpiece curved-tip cartridge in order to elevate a distal end of the workpiece curved-tip cartridge relative to its proximal end.

2. The surgical apparatus of claim 1, wherein said proximal upper spring engages the workpiece curved-tip cartridge at a first longitudinal location and said proximal bottom spring engages the workpiece curved-tip cartridge at a second longitudinal location distal to said first longitudinal location.

3. The surgical apparatus of claim 1, wherein said cavity includes a peak defined in an upper surface therein and an unload ramp defined in said upper surface of said cavity, said unload ramp extending downward distally from said peak, and wherein said distal bottom spring biases a distal tip of the workpiece curved-tip cartridge into engagement with said peak.

4. The surgical apparatus of claim 3, wherein engagement between said loader and the workpiece stapler channel causes the distal end of the workpiece curved-tip cartridge to slide distally along said unload ramp, thereby causing the distal end of the workpiece curved-tip cartridge to move downward and seat into the workpiece stapler channel.

5. The surgical apparatus of claim 1, wherein said proximal upper spring includes a fin at its free end, said fin configured to engage the workpiece curved-tip cartridge.

6. The surgical apparatus of claim 1, wherein said distal bottom spring is biased upward against the distal segment of the workpiece curved-tip cartridge.

7. The surgical apparatus of claim 1, wherein said loader further comprises:

a tongue, and a ramp defined in a lower surface of said cavity at a proximal end thereof, a proximal end of said ramp adjoining a distal end of said tongue, said ramp extending upward in a distal direction.

* * * * *